(12) United States Patent
Tribble et al.

(10) Patent No.: US 8,140,351 B2
(45) Date of Patent: Mar. 20, 2012

(54) CENTRALIZED STERILE DRUG PRODUCTS DISTRIBUTION AND AUTOMATED MANAGEMENT OF STERILE COMPOUNDING STATIONS

(75) Inventors: Dennis Tribble, Ormond Beach, FL (US); Joel A. Osborne, Port Orange, FL (US); Abdul Wahid Khan, Lindenhurst, IL (US); Matthew Valentine, Ormond Beach, FL (US); Bhavesh Padmani, Port Orange, FL (US)

(73) Assignee: FHT, Inc., Englewood, CO (US)

( * ) Notice: Subject to any disclaimer, the term of this patent is extended or adjusted under 35 U.S.C. 154(b) by 1292 days.

(21) Appl. No.: 11/752,769

(22) Filed: May 23, 2007

(65) Prior Publication Data
US 2008/0195246 A1  Aug. 14, 2008

Related U.S. Application Data

(60) Provisional application No. 60/888,832, filed on Feb. 8, 2007.

(51) Int. Cl.
*G06Q 10/00* (2006.01)

(52) U.S. Cl. .............................. 705/2; 705/3

(58) Field of Classification Search .................. 705/2–3
See application file for complete search history.

(56) References Cited

U.S. PATENT DOCUMENTS

| | | | |
|---|---|---|---|
| 4,847,764 A * | 7/1989 | Halvorson | 700/231 |
| 5,737,539 A * | 4/1998 | Edelson et al. | 705/3 |
| 7,096,212 B2 | 8/2006 | Tribble et al. | |
| 7,734,478 B2 * | 6/2010 | Goodall et al. | 705/2 |
| 7,769,601 B1 * | 8/2010 | Bleser et al. | 705/3 |
| 2004/0260577 A1 * | 12/2004 | Dahlin et al. | 705/2 |

\* cited by examiner

*Primary Examiner* — Vivek Koppikar
*Assistant Examiner* — Rajiv Raj
(74) *Attorney, Agent, or Firm* — Leason Ellis LLP

(57) ABSTRACT

Central management of dose order preparation retrieves an unprocessed dose order record, selects a workstation from a set of workstations, forwards the order for conversion into a drug dosage form, and repeats the process for additional unprocessed dose order records. Depending on the operation type of the selected workstation (manual, automatic), protocol information concerning preparation of the dose order is selectively provided to the selected workstation. Interrogatable elements enable tracking of dose orders and dosage forms throughout preparation, storage and distribution cycles. Further methods enable rapid fulfillment by utilizing inventory ahead of drug order processing if suitable dosage forms exist in inventory records.

29 Claims, 3 Drawing Sheets

Figure 1:
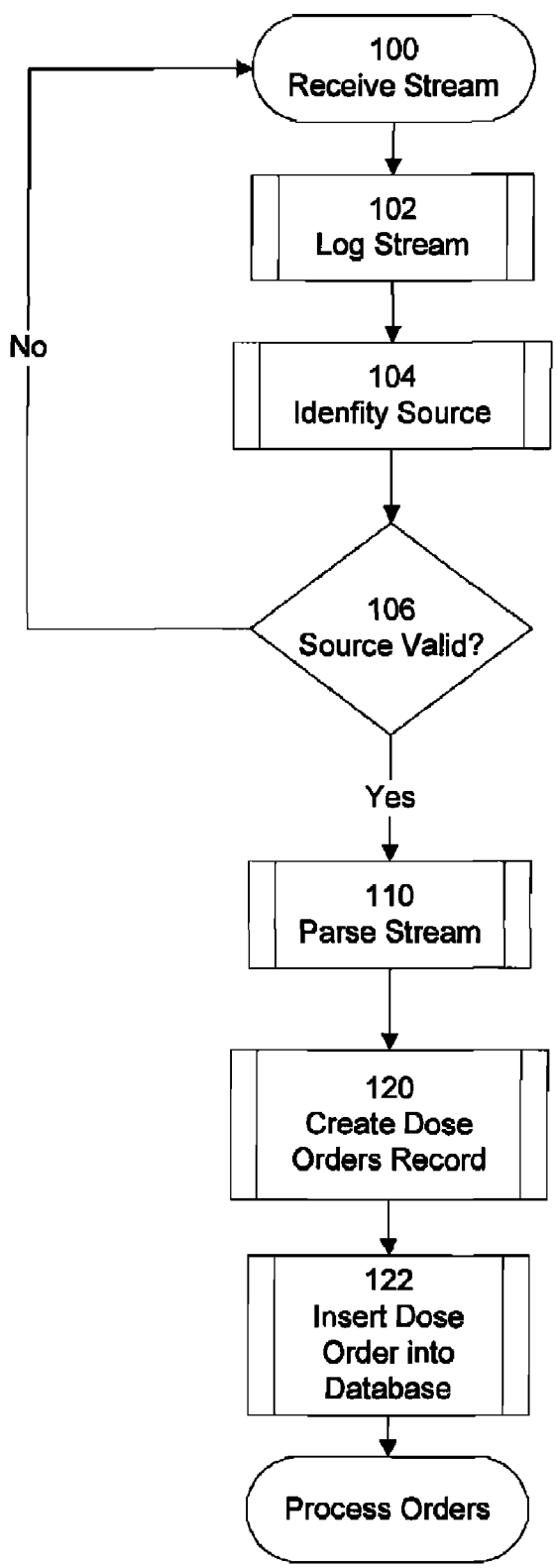

CENTRALIZED STERILE DRUG PRODUCTS DISTRIBUTION AND AUTOMATED MANAGEMENT OF STERILE COMPOUNDING STATIONS

FIELD OF THE INVENTION

The present invention relates to the management of medication dose orders and the environment within which the preparation of sterile doses occurs, and more particularly to some or all of the systems and steps taken in connection with the receipt, processing, filling, management, and distribution of medication dose orders and in connection with the management of medication preparation workstations.

BACKGROUND OF THE INVENTION

In many medical facilities medication orders are transmitted to a pharmacy from various locations throughout the hospital and by various means of communication. The process by which these medication orders are managed involves many discrete steps. Orders must be entered, transmitted and received by the pharmacy, validated, and filled according to manufacturer's specifications or established institutional guidelines. The filling process involves the selection and, where required, preparation of drug products for administration to patients in compliance with the validated order. Once filled, the resulting drug products (i.e., doses) must be delivered to the patient that requires them. One environment, by way of example, in which such transmissions and processes occur, is a hospital.

There are points in the process that are susceptible to miscommunication or loss of information. This can be problematic in terms of logging and auditing the processing and preparation of medications, which is often mandated by insurance and regulatory requirements. Additionally, there are inefficiencies associated with the present process and management of medication orders from the point of origination or to the point of consumption.

Physicians and other care providers order medications for hospitalized patients by generating medication orders in their patient record. When a pharmacy receives such an order, a pharmacist performs a variety of operational and clinical functions to ensure that the order is safe and appropriate and issues a medication dose order for the release of medications for administration to the patient. Current pharmacy practice limits the amount of that medication to that which is immediately needed both for reasons of patient safety and economics. Pharmacy computer systems regularly review the currently active medication orders, and generate additional medication dose orders as needed to maintain the patient supply. However, pharmacy computer systems do not provide preparation instructions to the sterile products compounding technician.

The pharmacy operationally receives these medication dose orders in the form of printed labels, typically generated by a hospital pharmacy computer system, one for each medication dose order to be dispensed. In many cases, a separate label is printed for each dose to be dispensed. Pharmacists and technicians use these labels as work documents to identify the medications to make and properly prepare and issue the desired medication. The labels are then used as address labels to ensure that the medications are routed to the correct patient for use. These labels lack detailed preparation steps, causing the technician to rely on his or her memory of the preparation procedures and guidelines, seek input from a co-worker, or find a manufacturer's package insert or a written institutional guideline.

One hazard of this method is that the label represents the only record of the work needing to be performed with the result that, if the label is lost or damaged, the work may not be performed (that is, the medication dose order may not be fulfilled) and the omission does not become known until a caregiver complains because they cannot locate the medication, or because a patient experiences an adverse event because of omitted medication.

U.S. Pat. No. 7,096,212 for "Serial Data Capture and Processing" and U.S. Patent Application No. 2003/0097368 for "Data Transmission Capture in Support of Medication Preparation" describe technology for automating the preparation of medication dose orders in response to the printing of such labels, the entire disclosure of which is hereby incorporated by reference, as though set forth in its entirety. However, these systems do not manage the distribution of medication dose orders to the various pharmacy workstations at which they are to be prepared, nor do they track the distribution of the completed dose orders to the patient for whom they are intended.

While many medications can be prepared by automated systems containing "built in" knowledge of correct preparation procedures, there are still large numbers of medication dose orders that require manual preparation, or institutions whose size precludes the incorporation of automation technology. The information and knowledge regarding how to prepare the medication is typically transferred verbally from one person to another. Thus, if a clinician receives an order for which he is unaware of the correct procedure for fulfillment, the clinician would have to request assistance, and thereby acknowledge a lack of training for that particular task. However, seeking training can be a source of embarrassment or be perceived as an undesired delay, either scenario providing a potential basis for the clinician to potentially use an improper procedure for the preparation of a particular medication, significantly increasing the possibility of a serious medication error due to flawed preparation procedures. Repeated conduct in this regard can result in "self trained" experience in a manner which is inconsistent with published procedures for handling that medication. Typically, the correct procedures are defined and written in a manual or other documentation. However, there is currently no efficient way to present the relevant excerpt of the manual to the clinician in relation to the particular medication order to be processed.

Furthermore, after a doctor or nurse enters a medication order, determining the status of the order requires manual intervention. The progress of the order can not easily be determined. The order must be located, determined if it has been filled, then possibly located somewhere throughout a facility such as a hospital, which can be complicated further as the medication dose is being transferred to the patient or as patients are moved from one location to another (e.g., from the patient's room to physical therapy or a lab).

Workload management systems for hospitals and sterile products preparation are unsophisticated and incapable of properly managing the process, causing conflicts between the level of staffing provided and the level of work to be performed.

Finally, delivery of medication dose orders to patient care areas in a hospital is not well-controlled, sometimes resulting in care-givers in patient care areas in a hospital being unaware that medication they require for care of a given patient has been delivered to the medication storage area where they are rendering care. This can result in lost productivity in the pharmacy and in the patient care areas while the pharmacist and the care giver attempt to sort out whether or not a medication dose order of interest has been completed.

The present invention addresses one or more of these and other problems to provide a medication order management, fulfillment, and tracking system. As more and more automated dispensing devices are developed, there is additional value in a mechanism in accordance with the present invention for automatically routing medication dose orders generated by the hospital pharmacy computer system to the most appropriate automated or manual workstations in the pharmacy and then tracking them to ensure that they are completed and distributed to their intended recipients. As work is completed at and returned from these workstations, it is valuable to know that the medication dose orders are ready for distribution and to prompt pharmacy personnel to get them delivered to the patient care areas.

SUMMARY OF THE INVENTION

In accordance with one aspect of the invention, a method for centrally managing dose order preparation comprises the steps of retrieving a dose order record having an unprocessed status, selecting a workstation and forwarding the order for conversion into a drug dosage form, and repeating the steps for additional dose order records.

In accordance with a further aspect of the present invention, the operation type of the selected workstation is determined, and a protocol concerning preparation of the unprocessed dose order is selectively provided to the selected workstation based on the operation type of the selected workstation.

In further aspects in accordance with the foregoing method, the dosage form can support an interrogatable tag which can be scanned in order to link the dosage form, and optionally also its current location, to the dose order record. Also, the foregoing method can include the additional step of arranging a plurality of dose order records in accordance with a rule such as urgency, type (solid, oral, intravenous), or medication.

In accordance with another aspect of the invention, a method for centrally managing logistics of a dose order fulfillment comprises the steps of receiving a dose order having a first priority for completion, comparing the dose order against an inventory record of prepared drug doses for a match, and, in the event of the match, directing a person to a location associated with the matched, prepared drug dose, registering the retrieval of the prepared drug dose from the location for delivery to another location, updating the inventory record, and instructing the preparation of the dose order at a second station for completion at a priority which is not greater than the first priority.

A database of interactive Standard Operating Procedures can be utilized for each drug that might be anticipated as needing preparation. Such database can perform dose calculations and manipulations of final volume and dose of the drug in accordance with unique aspects of the specific dose being prepared.

In accordance with yet a further aspect of this invention, confirmations can be performed to ensure that a proper preparation procedure was followed.

The invention can further log the steps of preparation and confirmation to provide a way to review or audit a prepared dose to ensure that the preparation was performed properly and that the expected values were achieved. Additionally, the current status of a medication dose order can be queried and retrieved at any time from an associated workstation.

BRIEF DESCRIPTION OF THE DRAWING FIGURES

Figure 1A:
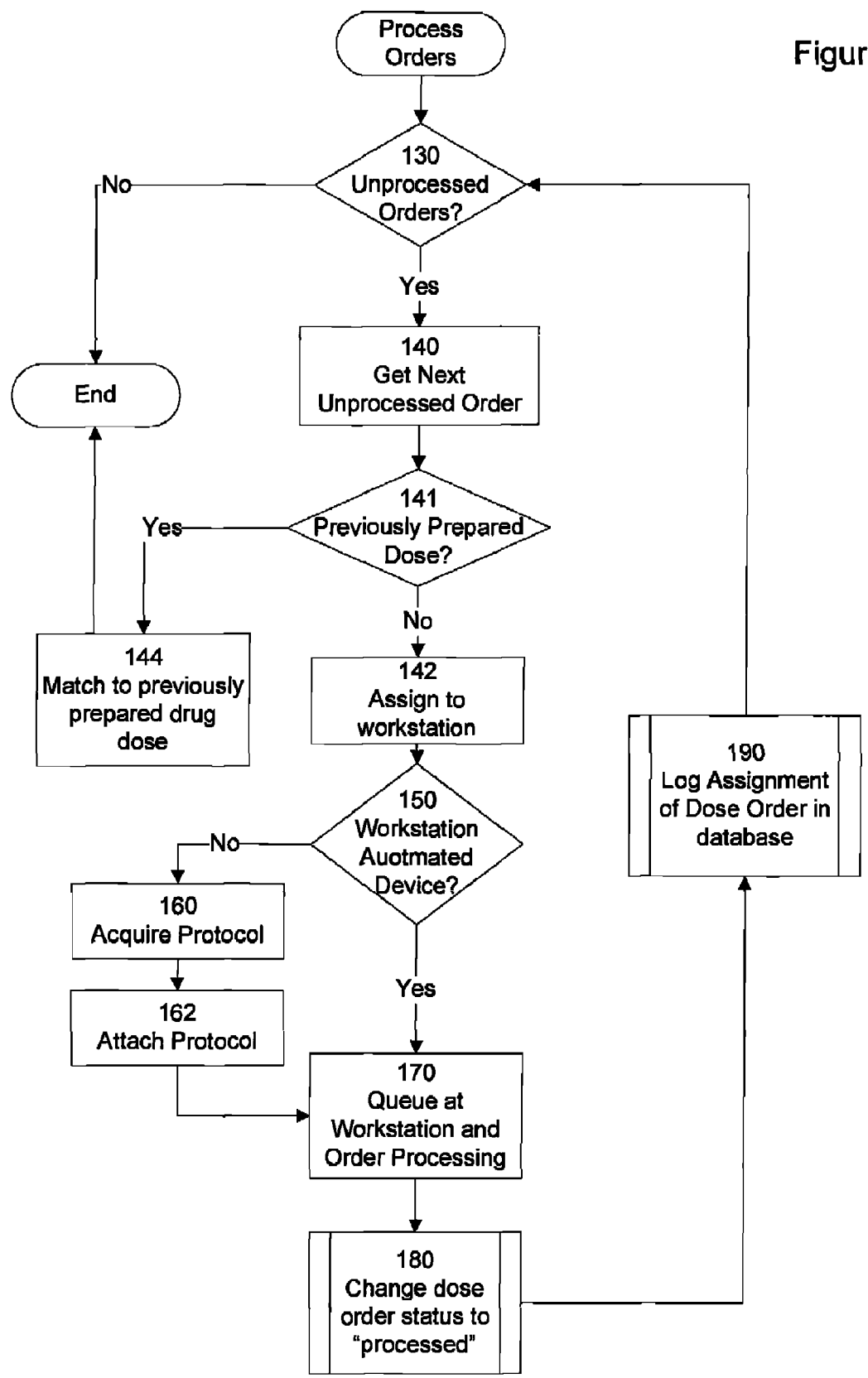
Figure 2:
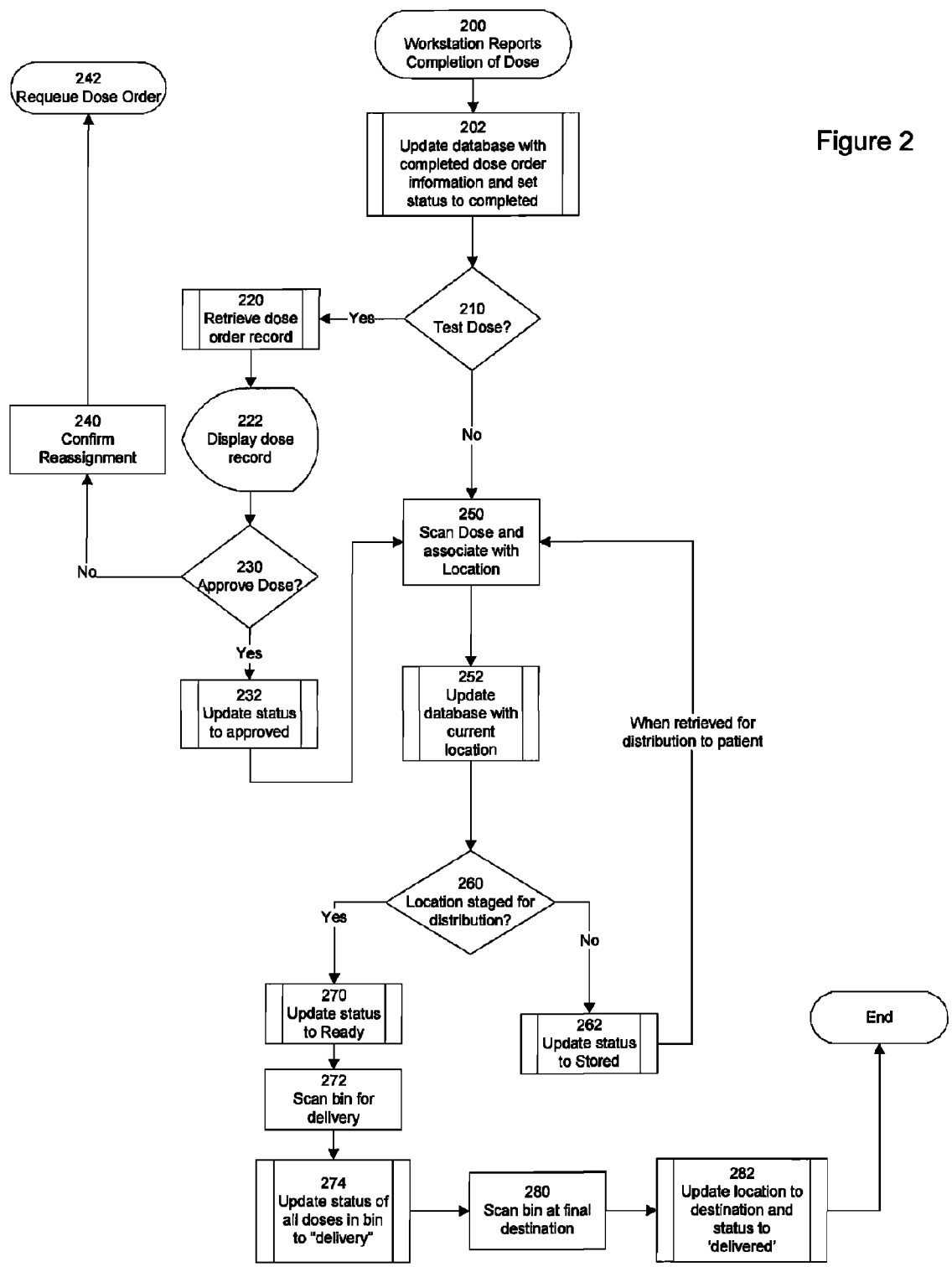

The foregoing and other features of the present invention will be more readily apparent from the following detailed description and drawings of the illustrative embodiments of the invention wherein like reference numbers refer to similar elements throughout the views and in which:

FIGS. 1 and 1A illustrate a process for receiving, processing, and preparing medication dose orders in accordance with one embodiment of the present invention; and FIG. 2 illustrates a process for managing and distributing prepared medication doses in accordance with an embodiment of the present invention.

DETAILED DESCRIPTION OF CERTAIN EMBODIMENTS

The present invention relates to the capture, processing, tracking, and distribution of medications. More particularly, the invention relates to an automated fulfillment system and method for receiving incoming medication dose orders, processing those orders, preferably in an efficient and optimized manner through the selective use of either an automated medication preparation fulfillment system or a manual medication preparation, and tracking the prepared medication dose through to its predetermined destination.

By way of overview and example, a doctor can enter one or more medication orders ("medication order") at a terminal in a hospital. The terminal can be connected via a network or to a computer system in the pharmacy. When the order is processed by the pharmacy computer system and labels for medication doses are generated, the data contained in the order and on the labels is captured, processed, and parsed by a computer implemented system to create individual medication dose orders ("dose order") and associated database records. The software managing the medication dose order processing distributes the orders to various compounding workstations (e.g., automated sterile compounding stations or manual processing stations) preferably in an optimized manner, as described below. At each stage of the order processing, the database record associated with the dose order is updated to reflect its status and location. Once the medication order is fulfilled, the resulting dose order is labeled preferably so as to associate it with a patient care location, represented in the pharmacy as a delivery container, such as a bin.

The association in the data record can be a result of linking the interrogation of a scanable element to the dose order record. A code supported by or secured to the dose itself and a code associated with the bin at the dosage form's current location can both be interrogated and then that information uploaded to a database. For example, the codes can be bar codes and can be sensed using a bar code scanner. The particular "scanner" used and the manner of "scanning" can be varied within the context of the invention to suit the requirements of a given implementation. Thus, for example, the code can be an optically scannable bar code or an interrogatable code such as an RFID tag that is supported in lieu of or in addition to bar codes, plain text, or other codes. The terms "scanner" and "scanning" are intended to include wireless interrogation or passive data reception whether they are based on an optical read, a radio frequency interrogation or an interrogation in some other frequency band, or a form of passive wireless data reception. More generally, the codes in scanable form are referred to as "tags."

As the dose is transported through the hospital to its final location, the bin is scanned and any new location is scanned at various points to track its progress through the hospital. If the dose is removed from the bin and placed into another bin, the new bin and the dose are scanned and associated in the database to correctly track the dose as it travels in the new bin. Once the dose reaches the point of consumption (e.g., the patient), the dose is removed from the bin and scanned so that its status can be updated as "delivered." Anyone with access to the system can track the progress of an order and determine its current location by inputting an identifier of the order. Furthermore, the fulfillment system provides complete oversight of the process from end to end for auditing and compliance purposes.

With reference now to FIG. 1, a process is illustrated by which orders are received, processed, and distributed within the pharmacy or medication preparation center. At step 100, medication order streams are received by the pharmacy. Order streams can be received through various methods. For example, a medication order can be entered into a computer terminal in communication with the pharmacy over a network. Alternatively, the medication data can be captured by a monitor device, such as a serial data monitor, a network monitor, or a software application monitor. Typically these order streams represent data intended to be printed on labels on a printer.

Medication order streams can contain a list of medication doses to prepare. Each dose order and dose is preferably associated with additional related data such as the patient for whom the medication is intended, by when it should be delivered, and to where it should be delivered. Further details can be associated with the medication including the prescribing doctor, the time and date the prescription was entered, the reason for medication, and other relevant information frequently recorded and associated with prescription.

Data streams containing medication dose data are preferably logged at step 102 by a monitoring computer. Preferably, streams are logged in a database or other computer accessible medium. Logging data streams enables extensive auditing and monitoring of the pharmacy—or hospital—dispensed medication. Because all data is logged, preferably in its raw form when it is first received by the pharmacy, no information is lost, corrupted, or disassociated during the processing or distribution of the medication. If necessary, an audit can be performed manually, off-line, or by a separate software program to reconstruct the data stream and all processing that should have or did occur after the pharmacy received the data stream. Furthermore, the logged data can be analyzed with respect to dose order demand. The average volume, peak volume, and standard deviation of dose orders can be determined for various historical time periods (e.g., day of the week, month, last week, last month, etc.). Based on this analysis, decisions regarding the required staffing to fulfill the expected volume of dose orders can be made.

Preferably, the data stream has an identifiable source. The source can be explicitly identified within the stream of data, or it can be determinable by the fulfillment system. Source determination can include, for example, examining TCP/IP packet or its header/footer information, examining cryptographic signatures of the stream, or data retrieved through additional network communication requesting the source. The source is identified at step 104.

At step 106, the fulfillment system determines whether the data stream originated from one of a set of valid sources. This can include identifying the source of the data stream and testing that it is one of the sources among those in the set. Validating the source ensures each medication dose prepared by the fulfillment system is legitimate and originating from an authorized prescribing entity. Alternatively, the validation can ensure that the prescribing entity is presently entitled to have its prescriptions filled by the pharmacy. If the source is not valid, the fulfillment system returns to step 100 to receive additional streams. Optionally, notifications can be sent to the source to inform it that there were validation issues or that the window for continued validation has one or more constraints (e.g., will expire in so-many days due to an overdue invoice).

In one embodiment of the fulfillment system, the software executes in a multi-threaded or multi-process environment. Thus, multiple streams can be processed simultaneously, by including necessary memory and database locks to ensure consistency. While the fulfillment system is described above as returning to step 100 to receive additional streams, persons of skill in the art appreciate that streams can be received by a server thread and dispatched for processing to other threads within a thread-pool. Other multi-threaded or multi-process mechanisms can be used to control the processing of data streams received by the fulfillment system.

After determining that the source is valid, the stream is parsed to extract relevant information at step 110. The fulfillment system can parse various message and data formats. Moreover, the parser can be extensible, such that as new formats are implemented or included within the networked environment, a parser extension can be included in the fulfillment system to parse the new format. For example, if the data stream is a serial printer data stream, the fulfillment system can determine the format of the data and pass the stream to the appropriate serial printer data parser. The printer data parser is configured to extract the dose medication contained within the stream. Preferably, the parser extracts all relevant data contained within the stream and maintains a record of the extracted data. The parsing methodology is preferably encapsulated in a library or set of modules that are called upon, as necessary, to parse a stream of any determined format. Each library entry or module operates as a "parser," as that term is used herein.

The data stream can contain one or more dose orders. For example, the stream may contain a single prescription dose request by a doctor for a single patient. Alternatively, the stream can include multiple dose orders for batch processing. The parser is preferably configured to recognize and discriminate between individual dose orders within a stream. The discrimination of individual dose orders can be accomplished by recognizing an order delimiter, or alternatively can be defined by the format of the data stream.

The data extracted by the parser at step 110 is used to create a dose order record at step 120. A dose order record is preferably created for each individual dose order encoded by the data stream, and contains the information extracted from the stream. At step 122 each dose order record can be stored in a database or other data storage system such as a suitable datastructure. Additionally, each dose order is preferably assigned a unique dose identifier that can be used to track the dose order and resulting dose through the fulfillment system.

The above description outlines the steps by which medication data streams enter the pharmacy and are pre-processed in anticipation of being filled by the pharmacy. Once the data streams have been processed, parsed into individual medication doses, and stored as dose records within the fulfillment system, the pharmacy can prepare the medication doses identified by each dose record.

Referring now to FIG. 1A, order fulfillment processing commences at step 130 at which the fulfillment system determines whether there are any unfulfilled medication doses in the database. If no unfulfilled orders exist, the fulfillment system can redirect its resources to processing incoming data streams at step 100, or completing or processing any active thread, as indicated schematically by the "end" terminator in the flow chart. However, if unfulfilled dose orders are in the database, the fulfillment system will retrieve an unfulfilled order at step 140. At decision 141, the system can determine whether a dose was previously prepared and stored which would satisfy the dose order. If no such dose exists, the dose order can be assigned to a medication preparation workstation at step 142.

Dose order records stored in the database can be ordered or arranged in accordance with one or more rules. For example, the rule can be to optimize fulfillment of the orders. For example, dose orders can be processed faster if the same medication is required because there is less cross-contamination and medication changes (i.e., retrieval and storage). Thus, dose orders can be grouped by type or medication, such that dose records requiring the same medication or with no risk of cross-contamination can be processed in order by the same machine, or set of machines. Alternatively, dose order records can be prioritized by urgency. For example, if a doctor urgently needs a specific medication, the data stream identifying the dose can include information indicating its urgency, and the dose order record can include such urgency information. Thus, an urgent order can be moved near the front of the queue, or identified as urgent and therefore receive immediate or expedited fulfillment. Through this or a similar mechanism, the next unfulfilled dose order retrieved at step 140 can be ordered to optimize throughput or to satisfy priorities.

Furthermore, as dose orders are received and parsed 110 or processed 140, the system can analyze the supplies necessary to fulfill the order. The list of required supplies can be compared to an inventory of supplies and their availability, optionally broken down by hospital, pharmacy location, or workstation. If there are insufficient supplies, additional supplies can be automatically ordered or the relocation of supplies from one workstation to another can be ordered such that at least one workstation will have the necessary supplies to fulfill the dose order.

Each dose order record initially has an unprocessed status and is operated upon by a particular workstation that is selected to convert the dose order into a particular drug dosage form in fulfillment of the order. A workstation can be adapted for a particular purpose, such as to include automated pill counters, automated syringe preparation, automated intravenous compounding stations, or be configured for manual preparation. By examining the dose order record, the fulfillment system can determine the appropriate workstation among available resources to which to assign the dose order at step 142, in view of the dosage order itself or its urgency, that is, its priority requirement for completion. The workstation assignment can further consider the supplies required to fulfill the dose order and the supplies available at each workstation. Also, at step 141, by examining the dose order record, the fulfillment system can determine whether a prepared dosage form is being stored, based on the contents of an inventory record, which can be matched to the dose order so as to fulfill that order, as indicated at step 144. In the event that a match is located, the further steps of FIG. 1A do not need to be performed in order to provide the source of the order with the requested dosage form; however, to prevent inventory depletion, the order can be processed at a priority (that is, in a time frame) that is less urgent than indicated in the order itself since the preparation of a drug dosage form based on the dose order is for the purpose of restocking the inventory. Also, in the event of a match, a person can be directed to a particular location associated with the drug dosage form so as to retrieve it from inventory, and the retrieval can be registered so that the inventory record can be updated to reflect that event.

It would be understood by one of skill in the art, that workstations can be located either centrally or in a distributed environment. Dose orders can be retrieved or sent to workstations via standard data messaging techniques. A centralized environment allows for the pooling of resources. However a distributed environment allows fulfillment to be completed closer to the end user and can reduce some of the inefficiencies of centralization.

At step 150 each dose order record can be examined to determine if it is appropriate for an automated workstation, or an operation type of a selected workstation can be determined, for example, based on a flag or other setting associated with the workstation such as availability and setup. If the dose order record is not appropriate for automated fulfillment, the order can be queued at a manual workstation and processed at step 170. However, before the dose order record is dispatched to a manual work station, additional information to facilitate the manual fulfillment of the dose is preferably provided to the selected workstation. This can be based on the determination that manual preparation is required and the assumption that providing additional information can improve safety, efficiency, and precision during fulfillment of the dose order. The additional information can be associated with the dose order record. For example, at step 160 the medication and form of dose (e.g., syringe, IV, etc.) specified by the dose order record can be examined so as to determine the protocol by which the dose of that medication should be prepared. The protocol can specify the steps (e.g., sanitization and documentation) that must be taken during preparation to comply with Food and Drug Administration regulations or any other governing procedures regarding the conduct of the pharmacy. Furthermore, the protocol associated with the dose order at steps 160 and 162, can guide the technician through the fulfillment process to achieve the same level of accuracy and dose safety which is typically associated with the automation. For example, the protocol can require the technician's input and process logging at critical stages of the dose preparation process (e.g., requiring the technician to scan information related to the source drug containers).

The additional information (i.e., protocol) can be associated with the dose order record at step 162. The association can be accomplished by attaching the protocol file to the dose order record, or otherwise communicating it electronically to the workstation selected for handling that dose order, or by printing a copy of the protocol to include with a printed order for the dose. In a paperless environment, the protocol is preferably displayed along with the display of the order or can appear as a hyperlink or call-up dialog box from within the order display.

The workstation can include various tools and monitoring equipment to assist and perform quality control during the manual preparation of the dose order. Such tools and monitoring equipment can include barcode scanners, digital cameras, scales, hydrometers, spectrometers, and other tools that can be used to verify the properties of a substance. For example, a computer monitor at the workstation can prompt the operator to take certain measurements of the dose order being prepared and input the results of those measurements. Failure to input a measurement within an acceptable range can result in the system automatically rejecting the preparation. Furthermore, to prevent operator fraud, the system can prompt the operator to place the preparation on a scale, or within another instrument, that automates the measurement, thereby reducing the opportunity for the operator to deceive the system.

Quality control can include the recordation and logging of any technician or operator involved in the preparation of a dose order. The identity of the technician or operator can be recorded by fingerprint, key-card, username, password, or other known methods of identification. Additionally, quality control tasks can be assigned to specific workstations or operators, such as supervisors or quality control specialists.

If it is determined at step 150 that the dose order record is suitable for automated handling, it will be queued at an appropriate automated workstation. Queuing the dose order record at a workstation presents a further opportunity to optimize the distribution of orders within the pharmacy. For example, it may not be feasible to determine at step 140 an optimal organization of dose order records to ensure that dose order records requiring similar medications are queued at the same workstation. Thus, at step 170, a particular dose order can be queued at a work station that is known to be processing the same medication, or at a workstation at which a dose order involving the same medication was just queued. Re-ordering and queuing of dose orders can be very flexible if the urgency of the dose order is very low. For example, the dose orders can be queued in a less than optimal order with respect to time, but more efficient with respect to medication changes and cleanings to prevent cross-contamination. Optionally, the current workload and/or work distribution of dose orders to workstations can be tracked or monitored and presented to a user (e.g., presented on a centralized display) for management and performance monitoring.

Moreover, various quality assurance activities can be assigned to workstations. These activities can include mandatory cleaning, training sessions, or inventory procedures. They can be scheduled at a workstation based on necessity (e.g., if the workstation is determined to be "dirty"), passage of time (e.g., protocol can call for cleaning or training every two hours or two days), or by need (e.g., monitoring procedures determine that certain equipment is "dirty" or that a particular operator is making mistakes and requires additional training). As used herein, "dirty" refers to a station being in a queue for a cleaning.

Once the workstation fulfills the dose order, the status of the dose order record can be changed to indicate that it has been processed at step 180. The status change can be received by the fulfillment system as an acknowledgement that the drug dosage form has been prepared, or as a "processed-order" status, and this can further result in an update to the dose order record, the inventory record, or both of drug dosage forms prepared but not yet delivered. Additionally, data concerning the assignment of the dose order to the selected workstation and the completion of the dose order can be logged in the database. Logging information concerning which workstation processed the dose order, as indicated at step 190, enables the complete tracking of the order and prepared dose from its entry as data to the pharmacy to its delivery to the patient.

The foregoing discussion details the process by which a data stream containing medication dose order information enters the pharmacy and is fulfilled to produce the associated dose. The fulfillment system is further capable of responding to any status inquiries concerning a given dose order with order status (e.g., "unprocessed," "in-progress at {selected workstations}," "processed" and the like) and optionally a location (e.g., in bin A, on cart B, in pediatric ward, etc.). The fulfillment system is also capable of monitoring and tracking the prepared dose through to its delivery with additional status information (e.g., dispensation to the patient), as discussed next with reference to FIG. 2.

The workstation identifies the dose as completed at step 200, and the database is updated with completion information at step 202, providing a status change that can be referenced by persons outside of the pharmacy in response to a status inquiry, and by the system in managing the distribution of subsequent dose orders. The identification preferably associates a unique identifier with the dose. The database record associated with the identified dose can be marked as completed. Alternatively, various other subsystems can be notified of the completion of the dose. For example, a storage subsystem that tracks medication that is "on-hand" can be updated with the prepared dose's record. Additionally, a delivery subsystem can be notified that the prepared dose is completed and ready for delivery to its destination.

It can be beneficial, for example, to test randomly selected or specific prepared doses for correct preparation. At step 210 a determination is made as to whether the prepared dose should be tested for correctness. Some prepared doses (e.g., manually prepared doses) require verification. Procedurally, it can also be beneficial—or even required—to select a prepared dose and verify its proper preparation. Verification can be performed on a random sample or for each prepared dose.

If it is determined at step 210 that the prepared dose should be tested, the database record associated with that dose (e.g., as may be identified using the doses' unique identifier) is retrieved at step 220. The record can be retrieved by scanning a barcode or other machine readable indicia included on the dose's container. The barcode preferably codes the unique identifier associated with dose, and the database record associated therewith is accessed. Alternatively, other information sufficient to uniquely identify the dose can be entered, manually or by machine. Optionally, if a particular sample is identified as a test candidate, a duplicate dose order can be introduced into the dosage queue, or it can be re-queued as though never prepared, so that a replacement is prepared.

Preferably, barcode scanners, reconstitution stations, label printers and other devices can be connected to the network to facilitate tracking and processing of dose orders. If, for example, a barcode scanner is connected to the network via a wireless communication link (e.g., an IEEE 802.11 variant) or as a peripheral to a network connected computer, database records can be updated in real-time as doses are scanned. Alternatively, an offline barcode reader can cache the scanned information along with a timestamp of the scan to upload and synchronize data once it is connected to the network, for example via a dock.

The dose record is displayed at step 222 so that the pharmacist, or other qualified clinician, can compare the database record against the physical prepared dose. If, at step 230, the pharmacist does not approve the dose, for example because the quantity does not match the quantity indicated by the database record, the disapproval is preferably confirmed at step 240. The pharmacist can further confirm that the dose is to be reassigned for preparation by a workstation, and, at step 242, the dose order record associated with the prepared dose is re-queued in the database, so that the fulfillment system will process it at step 140.

In addition to re-queuing an order record for any reason, the fulfillment system can update the status of the order to "incomplete" or "unprocessed." Alternatively, it may be desirable to track the number of prepared orders that are disapproved and the data associated with those orders (e.g., the workstation assigned, the pharmacist assigned, the medications and other lab equipment used during preparation, etc.) In such a scenario, the database record can be marked as disapproved or rejected and stored for auditing at some future date. If the database record is marked as rejected and stored, a duplicate dose order that is marked as unfulfilled can be generated and re-queued in the fulfillment system for processing. Preferably, the duplicate dose order indicates that it is a re-order of a previously processed order, contains a link or way to identify the original database record, and includes the original parsed data including an association with the original data stream.

If the pharmacist approves the prepared dose after testing it at step 230, the database record is preferably updated to reflect that it was approved, as indicated at step 232. If the prepared dose was not tested or was tested and approved, that dose is associated with a location at step 250. Preferably, the association of the prepared dose and the location is accomplished by scanning the barcode included on the prepared dose and a barcode associated with the location where the dose is being stored, with that location being recorded in the database as indicated at step 252. By associating the dose with a location soon after the dose is prepared, the dose can be fully tracked by its location as it moves through the hospital or facility until it reaches its final destination, in the event that a status inquiry is received or the system polls for that information in connection with the processing or management of other tasks, such as by assigning additional orders to the workstation at which that dose was just completed.

The location to which the dose is scanned can be a distribution location or a storage location. Distribution locations can include bins, racks, carts, trays, or any storage mechanism that is used to transport doses to patients or remote locations. A storage location can include a refrigerator or cabinet in which commonly used medication doses that are prepared in anticipation of use are stored for quick access and distribution. At step 260, the fulfillment system determines whether the dose was associated with a storage location or a distribution location.

If the dose is staged for storage, the dose order record is updated at step 262 to reflect its status as "stored" and its storage location. Preferably the database maintains the stored doses and the associated dose record to track the inventory available without requiring dose preparation. Additionally, the dose record can include an expiration date, whereby if an urgent order that is received for a particular medication, the database can be searched for stored doses that have not expired. Thus, the dose can be delivered to the patient or doctor quickly by retrieving the stored dose and bypassing the preparation and filling stage. When the stored dose is retrieved for distribution (e.g., to fulfill a particular order) and removed from storage, its location is scanned again and marked in the database, by again performing steps analogous or the same as steps 250 and 252, for tracking of the dose through its delivery.

On the other hand, if the dose is staged for distribution, the dose order record is preferably updated to "ready." The "ready" status indicates to a delivery person or other staff person that the medication is ready to be delivered and administered to the patient. Thus, if a nurse or doctor checks on the status of a particular dose order, the user will be notified that the dose is ready and delivery can be expedited if necessary. Likewise, the system can access and use that status information in connection with the processing or management of other tasks.

When a staff member retrieves the bin in which the dose is stored, and thus begins the dose's journey to its final destination, the bin is scanned at step 272 and the status of the dose, and any other doses known to the system as being held in the bin, is updated to "in delivery" at step 274. The bin can be used to update the location of all doses contained therein. Thus, if the bin is moved to a centralized distribution center on another floor, when the bin arrives at the distribution center, the bin can be scanned again and its location updated to indicate the distribution center. Therefore, the last known location of every dose can be tracked.

Preferably, the last known person to control the location of the dose is also recorded. Tracking the person can be performed by assigning individuals their own scanner on a temporary or permanent basis or requiring a user to input a personal identifier whenever an item is scanned.

The bin, and all doses stored within the bin, travel through the facility and are preferably scanned at each location, until it reaches its final destination, and is scanned at step 280. Scanning can be performed manually or automatically. For example, if the item being tracked is bar-coded or includes a computer readable identifier, scanners, which can be located throughout the facility, can be used to scan the item as it travels. After being scanned, the location of the item associated with the bar-code can be automatically updated in the database. Alternatively, passive or active RFID tags can be used to track the items by locating throughout the facility automated sensors which can detect each item when it comes within range of one of the sensors. Upon detecting the item, the item's identification can be read (e.g., passively or actively) from the tag and its associated location updated in the database.

When the individual dose is removed from the bin so that it can be administered to the patient, it is scanned at step 282 and its status is update to "delivered." In a further aspect of tracking and accounting for medication doses, the dose can be scanned once it has been administered, or once administration has begun (e.g., in the case of an intra-venous drip in which administration occurs over a period of time.) Additionally, the patient to whom the dose is administered can be recorded to ensure the correct patient received the prescribed mediation. Preferably, the patient's record includes a barcode or other indicia that can be scanned and associated with the administration of the dose.

Information concerning the dose can also be gathered from virtual checkpoints during transport and even after being administered. For example, the dose can be scanned and associated with a particular infusion pump. Thereafter, data from the infusion pump can be transmitted to the system and associated with the dose.

Thus, the fulfillment system described above tracks a medication order from its point of origin to its point of consumption. The data collected as it progresses through the system enables very thorough auditing and monitoring of the system. Furthermore, the pharmacy can be operated more efficiently by managing multiple orders and multiple workstations so as to optimize order priority and physical preparation.

While the invention has been described in connection with a certain embodiment thereof, the invention is not limited to the described embodiments but rather is more broadly defined by the recitations in the claims below and equivalents thereof.

We claim:

1. A method for centrally managing dose order preparation, comprising the steps of:
    (a) retrieving at a monitoring computer a first dose order record, the first dose order record having an unprocessed status;
    (b) selecting a workstation from among a set of workstations, at least one being an automated workstation, to handle the first dose order record;

(c) forwarding the first dose order record to the automated workstation for conversion into a drug dosage form and for preparation of a dose;
(d) receiving at the monitoring computer from the selected workstation a processed-order status indication;
(e) updating the first dose order record to the processed-order status, wherein the updating step includes updating a location of the drug dosage form;
(f) comparing the first dose order record with the prepared dose; and
(g) based on a rejection of the prepared dose, updating the first dose order record as being rejected and generating a second dose order record having an unprocessed status; and
(h) repeating steps (a) to (g);
wherein the second dose order record indicates that it is a re-order of the first dose order record and includes a link to the first dose order record.

2. The method of claim 1, further comprising the steps of: determining an operation type of the selected workstation; and selectively providing a protocol concerning preparation of the first dose order record to the selected workstation based on the operation type of the selected workstation.

3. The method of claim 2, wherein the selected workstation has a manual operation type and wherein the protocol is provided in response to the operation type being the manual operation type.

4. The method of claim 3, further comprising the steps of: prompting an operator of the selected workstation to provide information input regarding the protocol; receiving the information input; and analyzing the information input to verify preparation in conformance with the protocol.

5. The method of claim 2, wherein the selected workstation has an automated operation type and wherein the selected protocol fails in view of the operation type being automated.

6. The method of claim 1, including the additional step of responding from the monitoring computer to any status inquiry concerning the first dose order record with the processed-order status.

7. The method of claim 1, wherein the updating step includes updating a location of the drug dosage form to be that of the selected workstation.

8. The method of claim 7, including the additional step of responding from the monitoring computer to any status inquiry concerning the first dose order record with the processed-order status and the location.

9. The method of claim 1, including the additional steps of: supporting a first interrogatable tag on the drug dosage form; and linking the first interrogatable tag to the first dose order record.

10. The method of claim 9, including the additional step of associating a current location of the drug dosage form with a location.

11. The method of claim 10, wherein the location has a second interrogatable tag and wherein the associating step comprises interrogating the first and second interrogatable tags and storing information associated with each response in the first dose order record.

12. The method of claim 1, wherein the retrieving step retrieves the first dose order record from at least one of a memory, a file, and a database.

13. The method of claim 1, wherein the selecting step updates the first dose order record to associate the first dose order with the selected workstation.

14. The method of claim 1, wherein the retrieving step receives a plurality of dose order records, and wherein the method includes the additional step of arranging the plural dose order records in accordance with a rule.

15. The method of claim 14, wherein the arranging step comprises grouping the plural dose order records by at least one of type and medication, wherein the dose order records in the group are all forwarded to the selected workstation.

16. The method of claim 14, including the additional step of identifying an urgency associated with one of the plural dose order records, wherein the urgent dose order record is forwarded to the selected workstation for conversion into a drug dosage form and for preparation of a dose with a higher priority for handling than any unprocessed dose order record that has been forwarded to the selected workstation.

17. The method of claim 14, further comprising the steps of: generating a supply-list identifying a plurality of supplies required to fulfill the plurality of dose order records; comparing the supply-list with an inventory of supplies; and ordering one or more of the plurality of supplies not in the supply-list.

18. The method of claim 1, including the additional steps of identifying a source of the first dose order record, testing the source against a set of valid sources, and proceeding with the selecting and forwarding steps based on a determination that the source is among the set of valid sources.

19. The method of claim 1, wherein the set of workstations comprises one or more remote workstations configured to receive dose orders over a network.

20. The method of claim 1, further comprising the step of forwarding a quality assurance activity to a selected workstation.

21. The method of claim 20, wherein the step of forwarding a quality assurance activity is performed in response to a rule.

22. The method of claim 1, further comprising the steps of: receiving at the monitoring computer a medication order containing one or more dose order records; logging the dose order records received; and determining a predicted volume of work orders and a staffing level required to perform the predicted volume.

23. A method for centrally managing dose order preparation, comprising the steps of:
receiving at a monitoring computer a medication order containing one or more dose order records;
assigning an unprocessed status to each dose order record among the received dose order records;
retrieving a first dose order record, the first dose order record having an unprocessed status;
selecting a workstation from among a set of workstations to handle the first dose order record;
forwarding the first dose order record to the selected workstation for preparation of a dose;
comparing the first dose order record with the prepared dose; and
based on a rejection of the prepared dose, updating the first dose order record as being rejected and generating a second dose order record having an unprocessed status;
wherein the second dose order record indicates that it is a re-order of the first dose order record and includes a link to the first dose order record.

24. The method of claim 23, including the additional steps of providing to the workstation a standard order process protocol suitable for confirming any dose preparation steps;
performing dose preparation; and confirming that the dose preparation conforms to the standard process protocol.

25. The method of claim 24, wherein the confirming step uses automated equipment to test the prepared dose once it has been processed at the workstation.

26. The method of claim 1, further including the step of: preparing the dose from the first dose order record and if the dose is delivered to a storage location, the first dose order record is updated to reflect its status as "stored" and the storage location is saved, the first dose order record including an expiration date of the dose, and the step of selecting the workstation includes searching storage locations for doses that have not expired and satisfy the requirements of the first dose order record.

27. The method of claim 1, wherein the step of updating the first dose order record to the processed-order status further includes at least one of the following steps:

updating the first dose order record to a "ready" status when the dose is staged and ready for distribution and administration to a patient;

updating the first dose order record to an "in delivery" status when the dose has been retrieved and is placed in a container and is in route to the patient, wherein a location of the container is monitored; and updating the first dose order record to a "delivered" status when the dose is removed from the container for administering to the patient.

28. The method of claim 23, wherein the second dose order record comprises a duplicate dose order record.

29. The method of claim 23, further comprising re-queuing the second dose order for processing.

* * * * *